United States Patent [19]

Russo et al.

[11] Patent Number: 4,731,462
[45] Date of Patent: Mar. 15, 1988

[54] ORGANOTIN COMPOUNDS CONTAINING FLUORINE USEFUL FOR FORMING FLUORINE-DOPED TIN OXIDE COATING

[75] Inventors: David A. Russo, Edison, N.J.; Georg H. Lindner, Vlissingen, Netherlands

[73] Assignee: M&T Chemicals Inc., Woodbridge, N.J.

[21] Appl. No.: 888,298

[22] Filed: Jul. 18, 1986

[51] Int. Cl.$^4$ ................................................ C07F 7/22
[52] U.S. Cl. ..................................... 556/105; 556/81; 556/90; 556/94; 427/376.2; 427/383.5; 427/419.2
[58] Field of Search ...................... 556/81, 90, 94, 105

[56] References Cited

U.S. PATENT DOCUMENTS 3,385,830  5/1968  Vom Orde et al. ............ 556/105 X
3,775,453  11/1973  Mazdiyasni et al. ............. 556/81 X
3,781,315  12/1973  Pepe et al. ............................. 556/81
3,836,444  9/1974  Codet et al. ........................ 556/94 X

OTHER PUBLICATIONS

J. Inorg. Nucl. Chem., vol. 18, pp. 169–171 (1976).
J. Inorg. Nucl. Chem., vol. 35, pp. 1827–1831 (1973).
Chemical Abstracts, 79, 60994t (1973).
Chemical Abstracts, 78, 111453e (1973).
Chemical Abstracts, 77, 74427f (1972).
Chemical Abstracts, 84, 98669g (1976).

*Primary Examiner*—Helen M. S. Sneed
*Attorney, Agent, or Firm*—S. H. Parker; R. E. Bright

[57] ABSTRACT

This invention relates to organotin compounds containing fluorine which are particularly useful for forming fluorine-doped tin oxide coatings by the chemical vapor deposition method. In the preferred embodiment, the compound is monobutyldichlorotin trifluoroacetate, which is prepared by reaction of monobutyltin trichloride and trifluoroacetic acid.

8 Claims, No Drawings

ORGANOTIN COMPOUNDS CONTAINING FLUORINE USEFUL FOR FORMING FLUORINE-DOPED TIN OXIDE COATING

BACKGROUND ON THE INVENTION

1. Field of the Invention

This invention relates to organotin compounds containing fluorine which are useful in forming fluorine-doped tin oxide coatings.

2. Description of the Prior Art

The following are prior art references which describe compounds related to those of the present invention, which, however, do not have the attributes required to form liquid coating compositions for chemical vapor deposition.

Menke, in U.S. Pat. No. 3,759,743, described the preparation of non-halogenated organotin trifluoroacetates, and compositions thereof in organic solvents, such as methyl ethyl ketone, for making fluorine-doped tin-oxide coatings by the spray solution method. These precursors, however, have a low volatility and are unsuitable for the more advantageous chemical vapor deposition process where no solvent is added.

Wang and Shreeve, in Chemical Communications (1970) page 151, and J. Organomet. Chem. 38 (1972) page 287, describe the preparation of dialkylchlorotin trifluoroacetates. Such compounds, unfortunately, are solids which cannot be used in chemical vapor deposition process.

Bost, et al., in U.S. Pat. No. 4,093,636, describes related non-fluorinated organotin compounds, which cannot be used to provide fluorine-doped tin oxide coatings.

Plum, et al., in U.S. Pat. No. 4,374,778, discloses fluoroorganotin compounds in which the fluorine atom is bonded directly to the tin atom.

Franz, et al., in U.S. Pat. No. 4,254,046, disclose dialkyltin difluorides for powder deposition of fluorine-doped tin oxide coatings.

Thompson in French Pat. No. 1,400,314 describes mono, di- and trialkyltin trifluoroacetates and their preparation.

Liberte, Reiff and Davidsohn, in Organic Preparation and Procedures 1 (3) 173–176 (1969), describe the preparation of dialkyltin polyfluoro carboxylates.

An article in J. Organomet. Chem., (3) 151 (1970), describes a dialkylchlorotin trifluoromethyl acetate.

J. Organomet. Chem. 3972 (1971) describes trialkyltin perfluoroalkyl oxides.

These references do not disclose an organotin precursor useful for chemical vapor deposition particularly from a liquid coating composition. Moreover, the references do not disclose an organotin compound which has a monoalkyl or related substituent and at least one chlorine atom attached directly to the tin atom, and at least one trifluoromethyl-containing constituent.

Accordingly, an object of this invention is to provide new and improved organotin compounds which may be used directly to form fluorine doped tin oxide coatings having a low sheet resistance.

Another object herein is to provide such compounds which may be used to prepare fluorine-doped tin oxide coatings such as by the chemical vapor deposition method.

Still another object herein is to prepare monoalkylchlorotin trifluoracetates and related compounds which can be used advantageously in liquid coating compositions for chemical vapor deposition of fluorine-doped tin oxide coatings.

SUMMARY OF THE INVENTION

The organo compounds containing fluorine of the invention have the general formula:

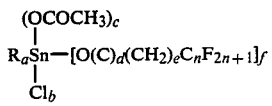

where
$R$ = alkyl, $C_1$–$C_6$; aryl; or carbalkoxyalkyl;
$a = 0, 1$;
$b = 1, 2, 3$;
$c = 0, 1$;
$d = 0, 1$;
$e = 0$–$2$;
$f = 1, 2$;
and
$n = 1$–$6$;
$a + b + c + d = 4$.

Table I below summarizes compounds of the invention within the general formula for each case of a, b, c, f, d, e and n in such formula. The reactants used in preparing such compounds also are given therein.

TABLE 1

| No. | a | b | c | f | d | e | n | Compound | Starting Materials Organotin Cmpd. | Fluorine Cmpd. |
|---|---|---|---|---|---|---|---|---|---|---|
| 1 | 1 | 1 | 0 | 2 | 0 | 0 | 2 | R—Sn(Cl)[OC$_2$F$_5$]$_2$ | 1 R—SnCl$_3$ + 2 —OC$_2$F$_5$ | |
| 2 | 1 | 1 | 0 | 2 | 0 | 0 | 4 | R—Sn(Cl)[OC$_4$F$_9$]$_2$ | 1 R—SnCl$_3$ + 2 —OC$_4$F$_9$ | |
| 3 | 1 | 1 | 0 | 2 | 1 | 0 | 1 | R—Sn(Cl)[OCOCF$_3$]$_2$ | 1 R—SnCl$_3$ + 2 —OCOCF$_3$ | |
| 4 | 1 | 1 | 0 | 2 | 1 | 0 | 2 | R—Sn(Cl)[OCOC$_2$F$_5$]$_2$ | 1 R—SnCl$_3$ + 2 —OCOC$_2$F$_5$ | |
| 5 | 1 | 1 | 0 | 2 | 1 | 0 | 4 | R—Sn(Cl)[OCOC$_4$F$_9$]$_2$ | 1 R—SnCl$_3$ + 2 —OCOC$_4$F$_9$ | |
| 6 | 1 | 1 | 0 | 2 | 0 | 2 | 4 | R—Sn(Cl)[OCH$_2$CH$_2$C$_4$F$_9$]$_2$ | 1 R—SnCl$_3$ + 2 —OCH$_2$CH$_2$C$_4$F$_9$ | |
| 7 | 1 | 1 | 0 | 2 | 1 | 1 | 4 | R—Sn(Cl)[OCOCH$_2$C$_4$F$_9$]$_2$ | 1 R—SnCl$_3$ + 2 —OCOCH$_2$C$_4$F$_9$ | |
| 8 | 1 | 1 | 1 | 1 | 0 | 0 | 2 | R—Sn(Cl)(OCOCH$_3$)[OC$_2$F$_5$] | 1 R—SnCl$_3$ + 1 —OC$_2$F$_5$ | + 1 —OCOCH$_3$ |
| 9 | 1 | 1 | 1 | 1 | 0 | 0 | 4 | R—Sn(Cl)(OCOCH$_3$)[OC$_4$F$_9$] | 1 R—SnCl$_3$ + 1 —OC$_4$F$_9$ | + 1 —OCOCH$_3$ |
| 10 | 1 | 1 | 1 | 1 | 0 | 0 | 1 | R—Sn(Cl)(OCOCH$_3$)[OCOCF$_3$] | 1 R—SnCl$_3$ + 1 —OCOCF$_3$ | + 1 —OCOCH$_3$ |
| 11 | 1 | 1 | 1 | 1 | 1 | 0 | 2 | R—Sn(Cl)(OCOCH$_3$)[OCOC$_2$F$_5$] | 1 R—SnCl$_3$ + 1 —OCOC$_2$F$_5$ | + 1 —OCOCH$_3$ |
| 12 | 1 | 1 | 1 | 1 | 1 | 0 | 4 | R—Sn(Cl)(OCOCH$_3$)[OCOC$_4$F$_9$] | 1 R—SnCl$_3$ + 1 —OCOC$_4$F$_9$ | + 1 —OCOCH$_3$ |
| 13 | 1 | 1 | 1 | 1 | 0 | 2 | 4 | R—Sn(Cl)(OCOCH$_3$)[OCH$_2$CH$_2$C$_4$F$_9$] | 1 R—SnCl$_3$ + 1 —OCH$_2$CH$_2$C$_4$F$_9$ | + 1 —OCOCH$_3$ |
| 14 | 1 | 1 | 1 | 1 | 1 | 1 | 4 | R—Sn(Cl)(OCOCH$_3$[OCOCH$_2$C$_4$F$_9$] | 1 R—SnCl$_3$ + 1 —OCOCH$_2$C$_4$F$_9$ | + 1 —OCOCH$_3$ |
| 15 | 1 | 2 | 0 | 1 | 0 | 0 | 2 | R—Sn(Cl)$_2$[OC$_2$F$_5$] | 1 R—SnCl$_3$ + 1 —OC$_2$F$_5$ | |
| 16 | 1 | 2 | 0 | 1 | 0 | 0 | 4 | R—Sn(Cl)$_2$[OC$_4$F$_9$] | 1 R—SnCl$_3$ + 1 —OC$_4$F$_9$ | |
| 17 | 1 | 2 | 0 | 1 | 0 | 0 | 1 | R—Sn(Cl)$_2$[OCOCF$_3$] | 1 R—SnCl$_3$ + 1 —OCOCF$_3$ | |
| 18 | 1 | 2 | 0 | 1 | 0 | 0 | 2 | R—Sn(Cl)$_2$[OCOC$_2$F$_5$] | 1 R—SnCl$_3$ + 1 —OCOC$_2$F$_5$ | |

TABLE 1-continued

| No. | a | b | c | f | d | e | n | Compound | Organotin Cmpd. | Fluorine Cmpd. |
|---|---|---|---|---|---|---|---|---|---|---|
| 19 | 1 | 2 | 0 | 1 | 0 | 0 | 4 | $R-Sn(Cl)_2[OCOC_4F_9]$ | $1\ R-SnCl_3 + 1\ -OCOC_4F_9$ | |
| 20 | 1 | 2 | 0 | 1 | 0 | 2 | 4 | $R-Sn(Cl)_2[OCH_2CH_2C_4F_9]$ | $1\ R-SnCl_3 + 1\ -OCH_2CH_2C_4F_9$ | |
| 21 | 1 | 2 | 0 | 1 | 0 | 1 | 4 | $R-Sn(Cl)_2[OCOCH_2C_4F_9]$ | $1\ R-SnCl_3 + 1\ -OCOCH_2C_4F_9$ | |
| 22 | 0 | 3 | 0 | 1 | 0 | 0 | 2 | $(Cl)_3-Sn[OC_2F_5]$ | $1\ SnCl_4 + 1\ -OC_2F_5$ | |
| 23 | 0 | 3 | 0 | 1 | 0 | 0 | 4 | $(Cl)_3-Sn[OC_4F_9]$ | $1\ SnCl_4 + 1\ -OC_4F_9$ | |
| 24 | 0 | 3 | 0 | 1 | 1 | 0 | 1 | $(Cl)_3-Sn[OCOCF_3]$ | $1\ SnCl_4 + 1\ -OCOCF_3$ | |
| 25 | 0 | 3 | 0 | 1 | 1 | 0 | 2 | $(Cl)_3-Sn[OCOC_2F_5]$ | $1\ SnCl_4 + 1\ -OCOC_2F_5$ | |
| 26 | 0 | 3 | 0 | 1 | 1 | 0 | 4 | $(Cl)_3-Sn[OCOC_4F_9]$ | $1\ SnCl_4 + 1\ -OCOC_4F_9$ | |
| 27 | 0 | 3 | 0 | 1 | 0 | 2 | 4 | $(Cl)_3-Sn[OCH_2CH_2C_4F_9]$ | $1\ SnCl_4 + 1\ -OCH_2CH_2C_4F_9$ | |
| 28 | 0 | 3 | 0 | 1 | 1 | 1 | 4 | $(Cl)_3-Sn[OCOCH_2C_4F_9]$ | $1\ SnCl_4 + 1\ -OCOCH_2C_4F_9$ | |
| 29 | 0 | 2 | 0 | 2 | 0 | 0 | 2 | $(Cl)_2-Sn[OC_2F_5]_2$ | $1\ SnCl_4 + 1\ -OC_2F_5$ | |
| 30 | 0 | 2 | 0 | 2 | 0 | 0 | 4 | $(Cl)_2-Sn[OC_2F_5]_2$ | $1\ SnCl_4 + 1\ -OC_4F_9$ | |
| 31 | 0 | 2 | 0 | 2 | 1 | 0 | 1 | $(Cl)_2-Sn[OCOCF_3]_2$ | $1\ SnCl_4 + 2\ -OCOCF_3$ | |
| 32 | 0 | 2 | 0 | 2 | 1 | 0 | 2 | $(Cl)_2-Sn[OCOC_2F_5]_2$ | $1\ SnCl_4 + 2\ -OCOC_2F_5$ | |
| 33 | 0 | 2 | 0 | 2 | 1 | 0 | 4 | $(Cl)_2-Sn[OCOC_4F_9]_2$ | $1\ SnCl_4 + 2\ -OCOC_4F_9$ | |
| 34 | 0 | 2 | 0 | 2 | 0 | 2 | 4 | $(Cl)_2-Sn[OCH_2CH_2C_4F_9]_2$ | $1\ SnCl_4 + 2\ -OCH_2CH_2C_4F_9$ | |
| 35 | 0 | 2 | 0 | 2 | 1 | 1 | 4 | $(Cl)_2-Sn[OCOCH_2C_4F_9]_2$ | $1\ SnCl_4 + 2\ -OCOCH_2C_4F_9$ | |
| 36 | 0 | 2 | 1 | 1 | 0 | 0 | 2 | $(Cl)_2-Sn(OCOCH_3)\ [OC_2F_5]$ | $1\ SnCl_4 + 1\ -OC_2F_5$ | $+ 1\ -OCOCH_3$ |
| 37 | 0 | 2 | 1 | 1 | 0 | 0 | 4 | $(Cl)_2-Sn(OCOCH_3)\ [OC_4F_9]$ | $1\ SnCl_4 + 1\ -OC_4F_9$ | $+ 1\ -OCOCH_3$ |
| 38 | 0 | 2 | 1 | 1 | 1 | 0 | 1 | $(Cl)_2-Sn(OCOCH_3)\ [OCOCF_3]$ | $1\ SnCl_4 + 1\ -OCOCF_3$ | $+ 1\ -OCOCH_3$ |
| 39 | 0 | 2 | 1 | 1 | 1 | 0 | 2 | $(Cl)_2-Sn(OCOCH_3)\ [OCOC_2F_5]$ | $1\ SnCl_4 + 1\ -OCOC_2F_5$ | $+ 1\ -OCOCH_3$ |
| 40 | 0 | 2 | 1 | 1 | 1 | 0 | 4 | $(Cl)_2-Sn(OCOCH_3)\ [OCOC_4F_9]$ | $1\ SnCl_4 + 1\ -OCOC_4F_9$ | $+ 1\ -OCOCH_3$ |
| 41 | 0 | 2 | 1 | 1 | 0 | 2 | 4 | $(Cl)_2-Sn(OCOCH_3)\ [OCH_2CH_2C_4F_9]$ | $1\ SnCl_4 + 1\ -OCH_2CH_2C_4F_9$ | $+ 1\ -OCOCH_3$ |
| 42 | 0 | 2 | 1 | 1 | 1 | 1 | 4 | $(Cl)_2-Sn(OCOCH_3)\ [OCOCH_2C_4F_9]$ | $1\ SnCl_4 + 1\ -OCOCH_2C_4F_9$ | $+ 1\ -OCOCH_3$ |
| 43 | 0 | 1 | 1 | 2 | 0 | 0 | 2 | $Cl-Sn(OCOCH_3)\ [OC_2F_5]_2$ | $1\ SnCl_4 + 2\ -OC_2F_5$ | $+ 1\ -OCOCH_3$ |
| 44 | 0 | 1 | 1 | 2 | 0 | 0 | 4 | $Cl-Sn(OCOCH_3)\ [OC_4F_9]_2$ | $1\ SnCl_4 + 2\ -OC_4F_9$ | $+ 1\ -OCOCH_3$ |
| 45 | 0 | 1 | 1 | 2 | 0 | 0 | 1 | $Cl-Sn(OCOCH_3)\ [OCOCF_3]_2$ | $1\ SnCl_4 + 2\ -OCOCF_3$ | $+ 1\ -OCOCH_3$ |
| 46 | 0 | 1 | 1 | 2 | 0 | 0 | 2 | $Cl-Sn(OCOCH_3)\ [OCOC_2F_5]_2$ | $1\ SnCl_4 + 2\ -OCOC_2F_5$ | $+ 1\ -OCOCH_3$ |
| 47 | 0 | 1 | 1 | 2 | 0 | 0 | 4 | $Cl-Sn(OCOCH_3)\ [OCOC_4F_9]_2$ | $1\ SnCl_4 + 2\ -OCOC_4F_9$ | $+ 1\ -OCOCH_3$ |
| 48 | 0 | 1 | 1 | 2 | 0 | 2 | 4 | $Cl-Sn(OCOCH_3)\ [OCH_2CH_2C_4F_9]_2$ | $1\ SnCl_4 + 2\ -OCH_2CH_2C_4F_9$ | $+ 1\ -OCOCH_3$ |
| 49 | 0 | 1 | 1 | 2 | 0 | 1 | 4 | $Cl-Sn(OCOCH_3)\ [OCOCH_2C_4F_9]_2$ | $1\ SnCl_4 + 2\ -OCOCH_2C_4F_9$ | $+ 1\ -OCOCH_3$ |

Accordingly, the preferred compounds of the invention include:

| Compound | Formula |
|---|---|
| 1. Butyldichlorotin trifluoroacetate | $C_4H_9Cl_2SnOCOCF_3$ |
| 2. Butylchlorotin bis(trifluoroacetate) | $C_4H_9ClSn(OCOCF_3)_2$ |
| 3. Butylchlorotin Acetate trifluoroacetate | $C_4H_9ClSn(OCOCH_3)(OCOCF_3)$ |
| 4. Carbethoxyethyl-dichlorotin trifluoroacetate | $CH_3CH_2OCOCH_2CH_2Cl_2SnOCOCF_3$ |
| 5. Butyldichlorotin trifluoroethoxide | $C_4H_9Cl_2SnOCH_2CF_3$ |
| 6. Trichlorotin trifluoroacetate | $SnCl_3OCOCF_3$ |

DETAILED DESCRIPTION OF THE INVENTION

The compounds of the invention may be prepared as described below.

General Reaction Process

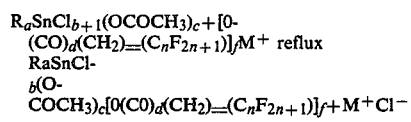

where $M^+$ is a cation.

The term "alkyl" as used herein includes straight and branched chain alkyl groups which have from one to six carbon atoms.

The term "organotin" compound as used herein includes tin tetrachloride.

Accordingly, representative organotin reactants used in preparing the compounds of the invention include monobutyltin trichloride, isobutylin trichloride, methyltin trichloride, dibutyltin dichloride, diisobutyltin dichloride, di-t-butyltin dichloride, butyldichlorotin acetate and carbethoxyethyltin trichloride; and tin tetrachloride.

The fluorine reactant has a trifluoromethyl group located alpha or beta to a functional group where carbon is bonded to oxygen, selected from carboxylic acid, anhydride, acid halide or alcohol.

Accordingly, suitable fluorine reactants include the following:

Carboxylic acids
trifluoroacetic acid
chlorodifluoroacetic acid
difluoroacetic acid
heptafluorobutyric acid
pentafluoropropionic acid
3-trifluoromethylcrotonic acid
nonafluoropentanoic acid Anhydrides
trifluoroacetic anhydride
heptafluorobutyric anhydride
pentafluoropropionic anhydride
chlorodifluoroacetic anhydride
perfluoroglutaric anhydride
perfluorosuccinic anhydride Acid Halides
heptafluorobutyryl chloride
perfluoroglutaryl fluoride
perfluoroctanoyl chloride
perfluorosuccinyl chloride Alcohols
2,2,2-trifluoroethanol
1H,1H-heptafluorobutanol-1
3,3,4,4,5,5,5-heptafluoropentanol-2
heptafluoroisopropanol
hexafluoro-2-methylisopropanol
1H,1H,5H-octafluoro-1-pentanol perfluoro-t-butanol
2-trifluoromethylpropanol-2
1,1,1-trifluoropropanol-2
perfluoroethanol In the preferred embodiment of the invention, monobutyltin trichloride is reacted with a salt of trifluoroacetic acid to form butyldichlorotin trifluoroacetate.

The invention will be illustrated by the following examples.

EXAMPLE 1

Reaction Product of Monobutyltin Trichloride and Trifluoroacetic Acid-Preparation of Monobutyldichlorotin Trifluoroacetate

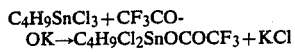

$C_4H_9SnCl_3 + CF_3COOK \rightarrow C_4H_9Cl_2SnOCOCF_3 + KCl$

A. A reaction mixture of monobutyltin trichloride, (MBTC) (8.46 g, 0.03 moles, 71.2 wt.%), and trifluoroacetic acid (TFA) (3.42 g, 0.03 moles, 28.8 wt.%), KOH (2.08 g., 0.03 moles), 15 ml. $H_2O$, 50 ml. ether, 50 ml. methylethyl ketone (MEK) and 0.1 g. of $C_{16}H_{33}(CH_3)_3N_+Br^-$ as phase transfer catalyst ($N^+Br^-$) was prepared by dissolving the KOH in water, and adding TFA; separately charging the MBTC, ether and MEK, and adding the $N^+Br^-$: thereafter adding the second solution to the first solution; heating to reflux while stirring under a nitrogen blanket, and refluxing at 48° C. for 2 hours.

After standing overnight, water and organic phases formed; the water phase was a clear, colorless lower layer, and the organic phase was a clear, yellow upper layer. The organic layer was concentrated and the residue placed in a vacuum dessicator overnight. The yield was 9.60 g. of brown, viscous liquid monobutyldichloro trifluoroacetate (89% yield). Anal. Sn 33%, 36% actual; Cl. 20%, 21% actual.

B. A reaction mixture of monobutyltin trichloride (200 g., 0.7 moles) and the sodium salt of trifluoroacetic acid (10 g., 0.07 moles) were heated at 70° C. for 3 hours and allowed to stand overnight at room temperature. The sodium chloride by-product and unreacted sodium salt were filtered. A liquid coating composition of about 12 wt.% monobutyldichlorotin trifluoroacetate and 88 wt% monobutyltin trichloride was produced in situ.

EXAMPLE 2

Reaction Product of Monophenyldichlorotin Trichloride and Trifluoroacetic Acid Preparation of Monophenyldichlorotin Trifluoroacetate A reaction mixture of monophenyltintrichloride (9.0 g., 0.03 moles) and the sodium salt of trifluoroacetic acid (3.42 g., 0.03 moles) was prepared as in Example 1 and refluxed for 2 hours to yield 81% of the desired product.

EXAMPLE 3

The experiment of Example 2 was repeated using the ammonium salt of trifluoroacetic acid with similar results.

EXAMPLE 4

Preparation of Fluorine-Doped Tin Oxide Coatings

The liquid coating composition of Example 1B was used for preparing fluorine-doped tin oxide coating on glass by chemical vapor deposition. Transparent, haze-free coatings of a thickness of 200 nm were obtained in 2 seconds deposition time at 650° C. in a water-containing air atmosphere. The sheet resistance was about 40 ohms per square; the infrared reflectivity was greater than 70% at 10 microns, and the visible light tranmission was greater than 70%.

We claim:

1. A compound having the formula:

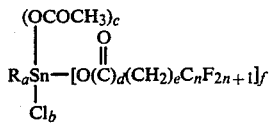

where:
R is alkyl; aryl or carbalkoxyalkyl;
$a = 1$
$b = 1, 2, 3$
$c = 0, 1$
$d = 0, 1$
$e = 0-2$
$f = 1, 2$
$n = 1-6$,
and
$a + b + c + d = 4$.

2. A compound according to claim 1 where R is alkyl $C_1-C_6$.

3. A compound according to claim 1 which is butyldichlorotin trifluoroacetate.

4. A compound according to claim 1 which is butyldichlorotin bis-trifluoroacetate.

5. A compound according to claim 1 which is butyldichlorotin acetate trifluoroacetate.

6. A compound according to claim 1 which is carbethoxyethyldichlorotin trifluoroacetate.

7. A compound according to claim 1 which is butyldichlorotin trifluoroethoxide.

8. A compound which is trichlorotin trifluoroacetate.

* * * * *

UNITED STATES PATENT OFFICE
CERTIFICATE OF CORRECTION

Patent No. 4,731,462                     Dated    3/15/88

Inventor(s)    David A. Russo and Georg H. Lindner

It is certified that error appears in the above-identified patent and that said Letters Patent are hereby corrected as shown below:

col. 2, line 45 and col. 6, line 40 change "d" to ---f---.

Signed and Sealed this

Thirteenth Day of September, 1988

*Attest:*

DONALD J. QUIGG

*Attesting Officer*   Commissioner of Patents and Trademarks

UNITED STATES PATENT OFFICE
CERTIFICATE OF CORRECTION

Patent No. 4,731,462        Dated 3/15/88

Inventor(s) David A. Russo and Georg H. Lindner

It is certified that error appears in the above-identified patent and that said Letters Patent are hereby corrected as shown below:

col. 2, lines 30-34, change the general formula to read:

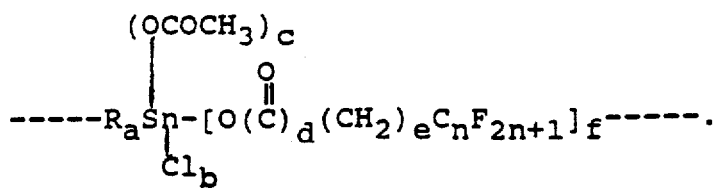

col.    lines 55 and 56 in the formulas change "$(CH_2)_=$" to read -----$(CH_2)_e$-----.

col. 5, line 49 change "Monophenyldichlorotin" to read----- Monophenyltin-----.

UNITED STATES PATENT AND TRADEMARK OFFICE
CERTIFICATE OF CORRECTION

PATENT NO. : 4,731,462
DATED : March 15, 1988
INVENTOR(S) : David A. Russo and Georg H. Lindner It is certified that error appears in the above-identified patent and that said Letters Patent is hereby corrected as shown below:

Col. 6, lines 45 and 47 change "butyldichlorotin" to read --butylchlorotin--.

Signed and Sealed this

Twenty-second Day of November, 1988

Attest:

DONALD J. QUIGG

Attesting Officer

Commissioner of Patents and Trademarks